United States Patent
Lal et al.

(12)

(10) Patent No.: US 6,479,645 B1
(45) Date of Patent: Nov. 12, 2002

(54) SULFURPENTAFLUORIDE COMPOUNDS AND METHODS FOR MAKING AND USING SAME

(75) Inventors: Gauri Sankar Lal, Whitehall; Kristen Elaine Minnich, Allentown, both of PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 10/104,214

(22) Filed: Mar. 22, 2002

(51) Int. Cl.[7] .................................................. C07F 7/08
(52) U.S. Cl. .................................. 532/427; 252/299.01
(58) Field of Search ....................... 556/427; 252/299.01

(56) References Cited

U.S. PATENT DOCUMENTS

| | | | |
|---|---|---|---|
| 4,053,497 A | * 10/1977 | Fory et al. | 556/427 |
| 4,652,664 A | * 3/1987 | Singer et al. | 556/427 |
| 4,749,803 A | * 6/1988 | Dowbenko et al. | 556/427 |
| 5,728,319 A | 3/1998 | Matsui et al. | 252/299.63 |
| 5,792,386 A | 8/1998 | Matsui et al. | 252/299.01 |
| 6,136,838 A | 10/2000 | Chern et al. | 514/404 |

FOREIGN PATENT DOCUMENTS

| | | |
|---|---|---|
| DE | 0444822 | 9/1994 |
| DE | 19748109 | 5/1999 |

OTHER PUBLICATIONS

"Syntheses and Characterizations of . . . ", Kovacina, et al, Ind. Eng. Chem. Prod. Res. Dev. 1983, 22, 2, 170.
"Synthesis and Chemistry of Ethynylsulfur . . . ", Hoover and Coffman, J. Am. Chem. Soc. 1964, 29, 3567.
"Synthesis and Spectroscopic Properties of . . . ", Canich, J.M., Inorg. Chem. 1985, 24, 3668.
"Derivatives of the Acetylenes HC C–SF5 and . . . ", J. Wessel, et al, Chem. Ber. 1986, 119, 45.

* cited by examiner

*Primary Examiner*—Paul F. Shaver
(74) *Attorney, Agent, or Firm*—Geoffrey L. Chase

(57) ABSTRACT

A sulfurpentafluoride and substituted silyl ethyne compound that is useful as precursors for a variety of organic compounds are disclosed. At least one of the substituents on the silicon atom is hindered. Also disclosed are high-yielding processes for making the ethyne compound of the present invention.

19 Claims, No Drawings

SULFURPENTAFLUORIDE COMPOUNDS AND METHODS FOR MAKING AND USING SAME

BACKGROUND OF THE INVENTION

The present invention relates generally to sulfurpentafluoride compounds having a substituted silyl group wherein at least one of the substituents is hindered and methods for making and using same. This invention also relates to the use of these compounds, for example, as precursors to liquid crystal components, surfactants, bioactive compounds in agrochemical and pharmaceutical compositions, or in polymers.

The development of synthetic methodologies for the introduction of sulfurpentafluoride or pentafluorosulfuranyl groups ("$SF_5$") into organic compounds has been pursued with a considerable degree of interest by several research groups. It is believed that the $SF_5$ group may impart unique properties to these organic compounds that include, inter alia, low surface energy, high chemical resistance, high thermal stability, high electronegativity, hydrophobicity, and high dielectric constant. For instance, the high electronegativity value of the $SF_5$ group, 3.62 on the Pauling scale, and greater electron withdrawing ability may make it an attractive alternative for the trifluoromethyl group ("$CF_3$") found in many commercial products.

Organic compositions containing $SF_5$ have been used in a variety of applications. For example, EP 444822, issued to Hansen and Savu describes pentafluorosulfuranyl fluoroaliphatic compositions that are used as surfactants. The reference, Kovacina et. al., Ind. Eng. Chem. Prod. Res. Dev. 1983, 22, 2, 170, describes $SF_5$-containing polymers that are prepared from mono and bis (pentafluorosulfur)-substituted diacetylenes. These polymers are soluble in fluorinated solvents and are not shock sensitive in comparison to the hydrocarbon analog. U.S. Pat. No. 6,136,838 describes sulfur pentafluorophenyl pyrazoles that are used for the control of ecoparasitic infections. Lastly, DE 19748109 issued to Kirsch et. al ("Kirsch") describes the preparation of several sulfurpentafluoride derivatives which are used to prepare liquid-crystal media.

Ethynylsulfur pentafluoride ($SF_5CCH$) has been oftentimes used as a synthetic intermediate or delivery vehicle for the introduction of the $SF_5$-moiety into complex organic compounds. Current methods to isolate $SF_5CCH$ have only been achieved in small scale, multi-step reactions. See, e.g., Hoover and Coffman, J. Am. Chem. Soc. 1964, 29, 3567 ("Hoover"); Canich et. al. Inorg. Chem. 1985, 24, 3668 ("Canich"). Both Hoover and Canich describe four-step reactions to prepare $SF_5CCH$ from acetylene and either sulfur chloride or sulfur bromide pentafluoride. The yields from these reactions ranged from 9 to 19%. Canich also describes a method of isolating ethynylsulfur pentafluoride via dehydrobromination of $SF_5CH=CHBr$ with a 49% yield. In the first step, $SF_5CH=CHBr$ was prepared in 80% yield from the reaction of acetylene and $SF_5Br$ which took approximately 4 days and was conducted at 57° C. Based upon this, the expected yield of ethynylsulfur pentafluoride after completion of the second step would be approximately 39%. Dehydrohalogenation of the acetylene $SF_5CH=CHCl$ resulted in product yields of only 1–2% of the desired alkyne. The relatively low yields, inefficiency, and long cycle times may make these processes impractical for large-scale industrial applications. Moreover, the reaction of acetylene with $SF_5Br$ or $SF_5Cl$ at high temperatures may be explosive.

Ethynylsulfur pentafluoride may also be obtained by the desilylation of its trialkylsilyl derivative. See Wessel et. al. Chem. Ber. 1986, 119, 45 ("Wessel"). Like the aforementioned methods to isolate $SF_5CCH$, the trimethylsilyl derivative of ethynylsulfur pentafluoride is impractical to produce on an industrial scale. The trimethylsilyl derivative of ethynylsulfur pentafluoride prepared as described in Wessel was obtained with only a 12% isolated yield.

Accordingly, there is a need in the art to provide novel compounds that deliver the $SF_5$ group into an organic compound. Depending upon the application, there may be a further need to provide novel compounds that deliver a substituted silyl group to an organic compound. There is also a need in the art for safe industrial processes to make $SF_5$ synthetic intermediates at greater yields, less cycle time, lower process temperatures, less volatility, and in a single reaction vessel. Due to the difficulties in the art in isolating the trimethylsilyl derivative of ethynlsulfur pentafluoride, it is thus surprising and unexpected to produce novel substituted-silyl sulfurpentafluoride compounds at relatively high yields when at least one of the substituents of the silyl group is hindered.

All references cited herein are incorporated herein by reference in their entirety.

BRIEF SUMMARY OF THE INVENTION

The present invention is directed, in part, to sulfurpentafluoride-containing compounds having a substituted silyl group. Specifically, in one embodiment of the present invention, there is provided a compound of the formula:

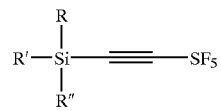

wherein the substitutents R, R', and R" may be an alkyl, a substituted alkyl, an aryl, a substituted aryl, or combinations thereof and at least one of the substitutents is hindered. In a preferred embodiment, R, R', and R" comprise isopropyl. In another preferred embodiment, R and ' comprise methyl and R" comprises t-butyl.

In a further embodiment of the present invention, there is provided a compound comprising a sulfurpentafluoride group and a substituted silyl group that is bonded to the sulfurpentafluoride group by a C—C triple bond. The substituted silyl group has substituents selected from the group consisting of an alkyl, a substituted alkyl, an aryl, a substituted aryl, or combinations thereof and at least one of the substituents is hindered. In another embodiment of the present invention, there are provided liquid crystal precursors that comprise the compounds of the present invention.

In yet a further embodiment of the present invention, there is disclosed a method for making a substituted silyl sulfurpentafluoride ethyne compound wherein the substituents on the silyl group are selected from the group consisting of an alkyl, a substituted alkyl, an aryl, a substituted aryl, or combinations thereof and at least one of the substituents is hindered. The method comprises the steps of: combining a substituted silyl acetylenic compound with a $SF_5$-containing halide under conditions sufficient to provide an intermediate product and exposing the intermediate product to a base under conditions sufficient to provide the ethyne compound. In certain preferred embodiments, the combining step is conducted in the presence of a solvent.

These and other aspects of the invention will become apparent from the following detailed description.

DETAILED DESCRIPTION OF THE INVENTION

The present invention is directed to sulfurpentafluoride-containing compounds having a substituted silyl group and methods for making and using same. The compounds of the present invention are suitable for use by themselves or in delivering sulfurpentafluoride groups and/or silyl groups to a variety of organic compositions. In addition, the methods of the present invention produce sulfurpentafluoride-containing compounds at production yields unattainable heretofore.

The compounds of the present invention comprise at least one sulfurpentafluoride grouping that is joined to a substituted silyl group via an unsaturated carbon bond. Preferably, the compound is an ethyne compound wherein the sulfurpentafluoride group is joined to the substituted silyl group via a C—C triple bond. At least one of the substituents on the silicon atom is hindered. The term "hindered" or "sterically hindered" as used herein relates to radical groups that impede or retard a given reaction with another molecule by virtue of its size. Some non-limiting examples of hindered alkyl groups include large primary (1°) alkyl groups such as octadecyl or nonadecyl; secondary (2°) alkyl groups such as isopropyl, isobutyl, or isopentyl; or tertiary (3°) alkyl groups such as tert-butyl ("t-butyl") or tert-pentyl ("t-pentyl").

In certain preferred embodiments, the sulfurpentafluoride-containing compound has the following formula:

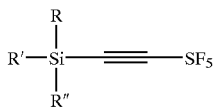

The silyl group within the compound is substituted, preferably trisubstituted, with radicals R, R', and R". Substituents R, R' and R" represent one or more substituents, like or different, that may comprise an alkyl group, a substituted alkyl group, an aryl group, a substituted aryl group, or combinations thereof. At least one of the substituents on the silicon atom is hindered.

As mentioned previously, subsituents R, R', and R" may be an alkyl or substituted alkyl group. The term "alkyl" as used herein includes straight chain, branched, or cyclic alkyl groups; preferably containing from 1 to 20 carbon atoms, or more preferably from 1 to 10 carbon atoms. This applies also to alkyl moieties contained in other groups such as haloalkyl, alkaryl, or aralkyl. The term "substituted alkyl" applies to alkyl moieties that have substituents that include heteroatoms such as O, N, S, or halogen atoms; $OCH_3$; OR (R=H, alkyl $C_{1-10}$, or aryl $C_{6-10}$); alkyl $C_{1-10}$ or aryl $C_{6-10}$; $NO_2$; $SO_3R$ (R=H, alkyl $C_{1-10}$, or aryl $C_{6-10}$); or $NR_2$ (R=H, alkyl $C_{1-10}$ or aryl $C_{6-10}$). The term "halogen" as used herein includes fluorine, chlorine, bromine, and iodine. In certain preferred embodiments, R, R', R" are individually 2° or 3° alkyl groups or combinations of 1°, 2°, and 3° alkyl groups with at least one 2° or 3° alkyl. Preferred substituents are when R, R', and R" are each isopropyl or when R and R' are $CH_3$ and R" are t-butyl.

The substitutents R, R', R" can also be an aryl or substituted aryl group. The term "aryl" as used herein six to twelve member carbon rings having aromatic character. The term "substituted aryl" as used herein includes aryl rings having subsitutents that include heteroatoms such as O, N, S, or halogen atoms; $OCH_3$; OR (R=H, alkyl $C_{1-10}$, or aryl $C_{6-10}$); alkyl $C_{1-10}$ or aryl $C_{6-10}$; $NO_2$; $SO_3R$ (R=H, alkyl $C_{1-10}$, or aryl $C_{6-10}$); or $NR_2$ R=H, alkyl $C_{1-10}$ or aryl $C_{6-10}$).

The compounds of the present invention are preferably prepared in a two-step process, as shown in Steps I and II below. This process may be performed in a single reaction vessel. This two-step process produced the desired product in excellent yield, from about 80% to about 99% of the theoretical yield, when at least one of the substituents on the silicon atom is hindered. By contrast, when the substituent on the silicon atom is relatively unhindered such as, for example, $CH_3$, the product is obtained in lower yield due to the cleavage of the silyl group during the second or elimination step. In Step I, a substituted silyl acetylene, preferably a trisubstituted silyl acetylene wherein at least one of the substituents is hindered, is reacted with a $SF_5$-containing halide to form a vinylic pentafluorosulfuranyl intermediate. The substituents on the silicon atom can be any of the substituents disclosed herein. In Step II, the hydrogen and halide within the vinylic pentafluorosulfuranyl intermediate is eliminated in the presence of a base to form the final product.

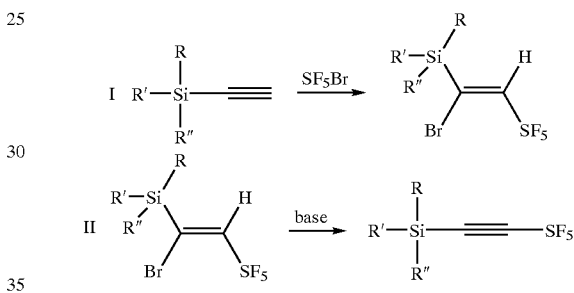

The first step of the process involves the reaction of a substituted silyl acetylenic compound with a $SF_5$-containing halide such as $SF_5Br$ or $SF_5Cl$ to produce an intermediate product which is an alkene bearing a halide atom and an —$SF_5$ group on adjacent carbons. At least one of the substituents on the silicon atom is hindered. This reaction may occur in the presence of a solvent. In embodiments where a solvent is used, the solvent selected will not react with the $SF_5$-containing halide or the intermediate product. Suitable solvents include, but are not limited to, hydrocarbons (e. g. pentane or hexane); halocarbons (e. g. Freon 113); ethers (e. g. ethylether ($Et_2O$) or tetrahydrofuran ("THF")); nitrites (e. g. $CH_3CN$); or aromatic compounds (e.g. benzotrifluoride). The reaction temperature may range from −78° C. to the boiling point of the solvent. The reaction time for the first step may range from about 0 hours or instantaneous to about 8 hours, preferably from about 0.1 to about 6 hours, or more preferably from about 0.5 to about 4 hours. The anticipated yield of the intermediate product ranges from about 80% to about 99% of the theoretical yield.

In the second or elimination step, the vinylic pentafluorosulfuranyl intermediate product of the first step is combined with a base to form the substituted silyl sulfurpentafluoride ethyne compound. The term "base" as used herein is any compound capable of exchanging negatively charged ions such as, but not limited to, hydroxide, halide, alkoxide, amide, organolithium, or organomagnesium ions. Examples of suitable bases include alkali metal and alkaline earth metal hydroxides. In some embodiments, the second step may be conducted in the presence of a solvent. Solvents that may be used in the second step include any of the solvents used in the first step as well as water. The temperature for the second step may range from −78° C. to the boiling point of the solvent. The reaction time for the second step may range from about 0 to about 24 hours or preferably from about 1 to about 16 hours. The anticipated yield of the ethyne compound ranges from about 80% to about 99% of the theoretical yield. The molecular weight of the ethyne compound ranges from about 225 to about 800 or more preferably about 225 to about 400. The final product may be purified by standard procedures such as distillation or chromatography.

The compounds of the present invention may be used as synthetic intermediates or starting reagents in any organic composition in which the organic composition requires the introduction of $SF_5$ and/or silyl groups into the composition. The compounds may be useful as a starting reagent for a number of derivatives that include, but are not limited to, saturated ethers, vinyl ethers, pyrazoles, cyclic alkenes, and $SF_5$-containing alkenes and alkynes. These compounds may also be used as an attractive alternative to reagents containing the $CF_3$ group. In this connection, the compounds of the present invention can be used as precursors within liquid crystal compositions such as those disclosed in U.S. Pat. Nos. 5,728,319 and 5,792,386 in place of those derivatives containing the $CF_3$ group. The substituted silyl group may be extracted during the preparation of the liquid crystal composition. The compounds of the present invention may also be used within surfactant compositions such as those described, for example, in EP 444822. Further uses for the compounds of the present invention include precursors or reagents within pharmaceutical compositions such as the compositions described, for example, in U.S. Pat. No. 6,136,838.

The compounds of the present invention can be incorporated within polymers such as polyacrylates, polyesters, polyurethanes, polyamides, and polyvinyl ethers made by conventional step-growth, chain-growth, or graft polymerization techniques or processes. In some instances, the ethyleneically unsaturated compounds of the present invention can be homopolymerized to make homopolymers or copolymerized with copolymerizable monomers to make random, alternating, block, or graft polymers. In these applications, for example, the silyl group of the compound may either be removed from the polymer composition prior to completion or may remain within the polymer to enhance certain properties of the polymer such as, for example, adhesive strength.

The invention will be illustrated in more detail with reference to the following examples, but it should be understood that the present invention is not deemed to be limited thereto. The gas chromatograph ("GC") analyses were carried out on a 30M RTX-5 column. The G.C.M.S. Spectra for the examples were performed on a Hewlett Packard 5890 Series 11 G.C. and 5972 series mass selective detector with a HP-5MS. The nuclear NMR analyses for the examples were obtained on a Bruker CP-300FT spectrometer operating at 282.4 MHz ($^{19}F$), 300.13 MHz ($^1H$). Chemical shifts were referenced to neat in $CFCl_3$($^{19}F$) and $CH Cl_3$ ($^1H$). The results for the examples are presented in Table I.

EXAMPLES

Comparative Example 1
$SF_5Br$ Addition to Trimethylsilylacetylene

A reaction mixture containing 20 mmole trimethylsilylacetylene, 10 mL Freon 113 and 17 mmole potassium fluoride was charged into a 30 mL stainless steel Parr reactor equipped with a magnetic stir bar. The reactor was connected to a stainless steel vacuum line equipped with two 300 cc stainless steel ballasts, pressure gauge, a soda-lime trap, and a vacuum pump. The reactor was degassed and cooled to −35° C. with a dry ice/acetone bath. A 25 mmole quantity of $SF_5Br$ was then condensed into the mixture. The reactor was sealed and allowed to warm to room temperature with stirring. After 3 hours, the reactor was vented and purged with $N_2$. The reaction mixture was slowly added to a cold sodium bicarbonate solution. The organic layer was isolated and the solvent was removed by rotary evaporation. The intermediate product, 1-bromo-1-trimethylsilyl-2-pentfluorosulfuranylethene, was shown to be 95% pure by gas GC analysis. The molecular weight of the intermediate was 305. The NMR results for the intermediate were as follows: $^1H$ NMR δ0.3 (s,9H), 7.5 (1H, m); $^{19}F$ NMR δ64 (4F,d), 80 (1 F,pent).

In the elimination step, a quantity of 20 mmole of the 1-bromo-1-trimethylsilyl-2-pentfluorosulfuranylethene intermediate was mixed with 25 mL decane and 60 mmole powdered potassium hydroxide and then stirred at room temperature for 17 hours. The solution was filtered. The solution contained 44% of the product,1-pentafluorosulfuranyl-2-trimethylsilylethyne, as determined by GC analysis. It is believed that when the substituent on the silicon atom is relatively unhindered, such as $CH_3$, the product is obtained in lower yield due to the cleavage of the silyl group during the second or elimination step.

The molecular weight of this product was 224. The NMR results for this product were as follows: $^1H$ NMR δ0.9 (9H,s); $^{19}F$ NMR δ75 (1F,pent), 80 (4F, d); GC/MS m/z=209 $(CH_3)_2SiC_2SF_5^+$; 127 $SF_5^+$; 89 $SF_3^+$.

Example 2
$SF_5Br$ Addition to t-butyldimethylsilylacetylene

The intermediate product, 1-bromo-1-t-butyldimethylsilyl-2-pentafluorosulfuranylethene was prepared as described above in Comparative Example 1 from an initial reaction mixture containing 20 mmole t-butyldimethylsilylacetylene, 10 mL Freon 113 and 17 mmole potassium fluoride. The intermediate product, 1-bromo-1-t-butyldimethylsilyl-2-pentafluorosulfuranylethene, was shown to be 98% pure by GC analysis. The molecular weight of the intermediate was 347. The NMR results for the intermediate were as follows: $^1H$ NMR δ0.35 s (6H), 1.0 s (9H), 7.6 (m,1H); $^{19}F$ NMR δ65 (4F, d), 80 (1F,pent).

In the elimination step, a quantity of 20 mmole of the 1-bromo-1-t-butyldimethylsilyl-2-pentafluorosulfuranylethene intermediate was mixed with 25 mL pentane and 60 mmole powdered potassium hydroxide and then stirred at room temperature for 17 hours. The solution was filtered and the solvent was removed by rotary evaporation.

The solution contained 97% of the product, 1-t-butyldimethylsilyl-2-pentafluorosulfuranylethyne, as determined by GC analysis. This yield is believed to be higher than Comparative Example I because one of the substituents on the silyl group is hindered. The product was further purified by vacuum distillation conducted at 0.5 Torr and room temperature with a dry ice/aetone bath at the receiver. The molecular weight of the product was 266. The NMR results for this product were as follows: $^1H$ NMR δ0.2 s, 0.9 s; $^{19}F$ NMR δ76 (1F,pent), 81 (4F,d); GC/MS m/z=266 $tBu(CH_3)_2SiC_2SF_5+$;247 $tBu(CH_3)_2SiC_2SF_4^+$; 209 $(CH_3)_2SiC_2SF_5^+$; 127 SF5; 57 $tBu^+$.

Example 3
SF$_5$Br Addition to Triisopropylsilylacetylene

The intermediate product, 1-bromo-1-triisopropylsilyl-2-pentafluorosulfuranylethene was prepared as described above in Comparative Example 1 from an initial reaction mixture containing containing 20 mmole triisopropylsilylacetylene, 10 mL Freon 113 and 17 mmole potassium fluoride. The intermediate, 1-bromo-1-triisopropylsilyl-2-pentafluorosulfuranylethene, was shown to be 90% pure by GC analysis. The molecular weight of this product was 389. The NMR results for this product were as follows: $^1$H NMR δ1.6(21H, m), 7.8 (1H, m); $^{19}$F NMR δ64 (4F, d), 80 (1F, pent).

In the elimination step, a quantity of 20 mmole of the 1-bromo-1-triisopropylsilyl-2-pentafluorosulfuranylethene product was mixed with 25 mL pentane and 60 mmole powdered potassium hydroxide and then stirred at room temperature for 17 hours. The solution was filtered and solvent was removed by rotary evaporation. The product, 1-pentafluorosulfuranyl-2-triisopropylsilylethyne, was shown to be 90% pure by GC analysis. This yield is believed to be higher than Comparative Example 1 because one of the substituents on the silyl group is hindered. The product was further purified by vacuum distillation conducted at 0.5 Torr and 26° C. The molecular weight of this product was 308. The NMR results for this product were as follows: $^1$H NMR δ1.1 (m,21H); $^{19}$F NMR δ76(1F, pent), 81 (4F,d); GC/MS m/z=308 (iPr)$_3$SiC$_2$SF$_{5+}$; 265 (iPr)$_2$SiC$_2$SF$_5^+$.

Example 4
SF$_5$Br Addition to Triisopropylsilylacetylene without Isolation of the Intermediate Product A reaction mixture containing 90 mmole triisopropylsilylacetylene and 140 mL pentane was charged into a 300 mL stainless steel Parr reactor equipped with a magnetic stir bar. The reactor was connected to a stainless steel vacuum line equipped with two 300 cc stainless steel ballasts, pressure gauge, a soda-lime trap, and a vacuum pump. The mixture was cooled to −35° C. with a dry ice/acetone bath and degassed. A 46 mmole quantity of SF$_5$Br was then condensed into the mixture. The reactor was sealed and allowed to warm to room temperature with stirring. After 1.5 hours, the reactor was again cooled to −35° C. and another 46 mmole SF$_5$Br was condensed into the mixture. After 2 hours, the reactor was vented and purged with N$_2$. The reaction mixture was slowly added to a cold sodium bicarbonate solution. The organic layer was isolated from the mixture. The intermediate product, 1-bromo-1-triisopropylsilyl-2-pentafluorosulfuranylethene, was shown to be 95% pure by gas GC analysis. Powdered potassium hydroxide, 276 mmole, was added to the organic layer containing the intermediate and stirred overnight. The solution was filtered and the solvent was removed by rotary evaporation. The product, 1-pentafluorosulfuranyl-2-triisopropylsilylethyne, was shown to be 95% pure by GC analysis. The molecular weight of this product was 308. The NMR results for this product were as follows: $^1$H NMR δ1.1 (m,21H); $^{19}$F NMR δ76(1F, pent), 81 (4F,d); GC/MS m/z=308 (iPr)$_3$SiC$_2$SF$_{5+}$; 265 (iPr)$_2$SiC$_2$SF$_5^+$.

TABLE I

| | Intermediate Product | Product | Product (% Yield) | Molecular Weight |
|---|---|---|---|---|
| Comp. Ex. 1 | (CH$_3$)$_3$Si—C(Br)=C(H)—SF$_5$ | (CH$_3$)$_3$Si—C≡C—SF$_5$ | 44% | 224 |
| Example 2 | tBu(CH$_3$)$_2$Si—C(Br)=C(H)—SF$_5$ | tBu(CH$_3$)$_2$Si—C≡C—SF$_5$ | 97% | 266 |
| Example 3 | (iPr)$_3$Si—C(Br)=C(H)—SF$_5$ | (iPr)$_3$Si—C≡C—SF$_5$ | 90% | 308 |
| Example 4 | (iPr)$_3$Si—C(Br)=C(H)—SF$_5$ | (iPr)$_3$Si—C≡C—SF$_5$ | 95% | 308 |

While the invention has been described in detail and with reference to specific examples thereof, it will be apparent to one skilled in the art that various changes and modifications can be made therein without departing from the spirit and scope thereof.

We claim:

1. A compound having the formula:

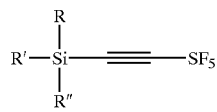

wherein substituents R, R', and R" are selected from the group consisting of an alkyl, a substituted alkyl, an aryl, a substituted aryl, or combinations thereof and at least one of the substituents is hindered.

2. The compound of claim 1 wherein R, R', or R" comprises an alkyl.

3. The compound of claim 2 wherein at least one of R, R', or R" comprises t-butyl.

4. The compound of claim 3 wherein R and ' comprises CH₃ and R" comprises t-butyl.

5. The compound of claim 2 wherein at least one of R, R', or R" comprises isopropyl.

6. The compound of claim 1 wherein the molecular weight of the compound ranges from about 225 to about 800.

7. The compound of claim 6 wherein the molecular weight of the compound ranges from about 225 to about 400.

8. A liquid crystal precursor comprised of the compound of claim 1.

9. A compound, the compound comprising:
   a sulfurpentafluoride group; and
   a substituted silyl group, having substituents selected from the group consisting of an alkyl, a substituted alkyl, an aryl, a substituted aryl, or combinations thereof and at least one of the substituents is hindered, wherein the substituted silyl group is bonded to the sulfurpentafluoride group by a C—C triple bond.

10. The compound of claim 9 wherein at least one of the substituents comprises an alkyl group.

11. The compound of claim 10 wherein at least one of the substituents comprises t-butyl.

12. The compound of claim 10 wherein at least one of the substituents comprises CH₃.

13. The compound of claim 10 wherein at least one of the substitutents comprises isopropyl.

14. A liquid crystal precursor comprised of the compound of claim 9.

15. A method for making an ethyne compound of the formula:

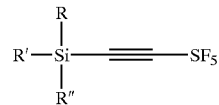

wherein the substitutents R, R', and R" are selected from the group consisting of an alkyl, a substituted alkyl, an aryl, a substituted aryl, or combinations thereof and at least one of the substitutents is hindered, the method comprising the steps of:
   combining a R, R', and R" substituted acetylenic compound with a SF₅-containing halide under conditions sufficient to form an intermediate product; and
   exposing the intermediate product to a base under conditions sufficient to form the ethyne compound.

16. The method of claim 15 wherein the combining and the exposing steps are performed in the same reaction vessel.

17. The method of claim 15 wherein the combining step is conducted in the presence of a solvent.

18. The method of claim 15 wherein a yield of the ethyne compound is at least about 80% of a theoretical yield.

19. The method of claim 17 wherein the yield of the ethyne compound is at least about 90% of the theoretical yield.

* * * * *

UNITED STATES PATENT AND TRADEMARK OFFICE
CERTIFICATE OF CORRECTION

PATENT NO.   : 6,479,645 B1
DATED        : November 12, 2002
INVENTOR(S)  : Gauri Sankar Lal et al.

It is certified that error appears in the above-identified patent and that said Letters Patent is hereby corrected as shown below:

Column 9,
Line 1, after "R and," insert -- R' --

Signed and Sealed this

Seventeenth Day of June, 2003

JAMES E. ROGAN
*Director of the United States Patent and Trademark Office*